United States Patent [19]

Anderson et al.

[11] Patent Number: 5,220,400
[45] Date of Patent: Jun. 15, 1993

[54] CONTAINER INSPECTION SYSTEM
[75] Inventors: Charles H. Anderson; Charles K. Harris, both of Dallas, Tex.
[73] Assignee: Texas Instruments Incorporated, Dallas, Tex.
[21] Appl. No.: 531,819
[22] Filed: Jun. 1, 1990
[51] Int. Cl.⁵ .............................................. G01N 21/88
[52] U.S. Cl. .................................... 356/241; 250/572
[58] Field of Search ............... 356/237, 240, 241, 236; 250/572, 223 B; 358/106; 350/525

[56] References Cited
U.S. PATENT DOCUMENTS

| | | | |
|---|---|---|---|
| 1,444,400 | 2/1923 | Silverman | 350/525 |
| 4,424,441 | 1/1984 | Bieringer et al. | 356/240 |
| 4,606,635 | 8/1986 | Miyazawa et al. | 358/106 |
| 4,695,157 | 9/1987 | Schoenbaum et al. | 356/237 |
| 4,924,107 | 5/1990 | Tucker et al. | 250/572 |
| 5,072,127 | 12/1991 | Cochran et al. | 358/106 |

Primary Examiner—Richard A. Rosenberger
Attorney, Agent, or Firm—Stanton C. Braden; Richard L. Donaldson

[57] ABSTRACT

A single camera container inspection system that views the entire interior surface of a container during one pass, producing a single image of the interior surfaces to detect defects and contaminants in the interior surfaces of the container.

9 Claims, 3 Drawing Sheets

CONTAINER INSPECTION SYSTEM

FIELD OF THE INVENTION

This invention relates to automated container inspection systems using machine vision, and more particularly to a single camera and illumination system for inspecting containers in a single pass.

BACKGROUND OF THE INVENTION

The inspection of container interiors, particularly beverage cans and other opaque containers requires imaging of all areas of the container from the top flange, past the sidewalls, to the bottom areas. Automated systems typically are required to inspect for 1 mm defects from the top to the bottom of the can. Prior art systems involve multiple inspection stations and/or multiple cameras focussed onto different sections of the can. These prior art systems require a high level of mechanical and optical complexity due to their multiple optics and camera stations. Critical alignments are necessary to combine several images or sectors into one composite to detect any and all defects in the can.

Diffused lighting systems have been used to light containers such as glass bottles, but in the multiple camera and multiple pass inspection systems, it is not necessary to have uniform lighting over the entire area to be inspected, only the area being inspected during the particular inspection pass.

SUMMARY OF THE INVENTION

The invention is an inspection system that can be used for opaque containers such as beverage and food cans. It is a single pass inspection system such that the entire inside surface of the can is uniformly illuminated and viewed during a single pass with a single high resolution camera with a wide angle lens.

A high resolution camera using a short focal length wide angle lens is used. The illumination system is a diffused illumination system that projects light into the can by reflection from a light source. It is important that no light is directed into the can direct from the light source itself. The diffusing surface and light source surrounds the camera lens. The manner in which the light source is diffused and structured causes it to be different from other approaches now in use.

The technical advance represented by the invention as well as the objects thereof will become apparent from the following description of a preferred embodiment of the invention when considered in conjunction with the accompanying drawings, and the novel features set forth in the appended claims.

DESCRIPTION OF A PREFERRED EMBODIMENT OF THE INVENTION

Figure 1:
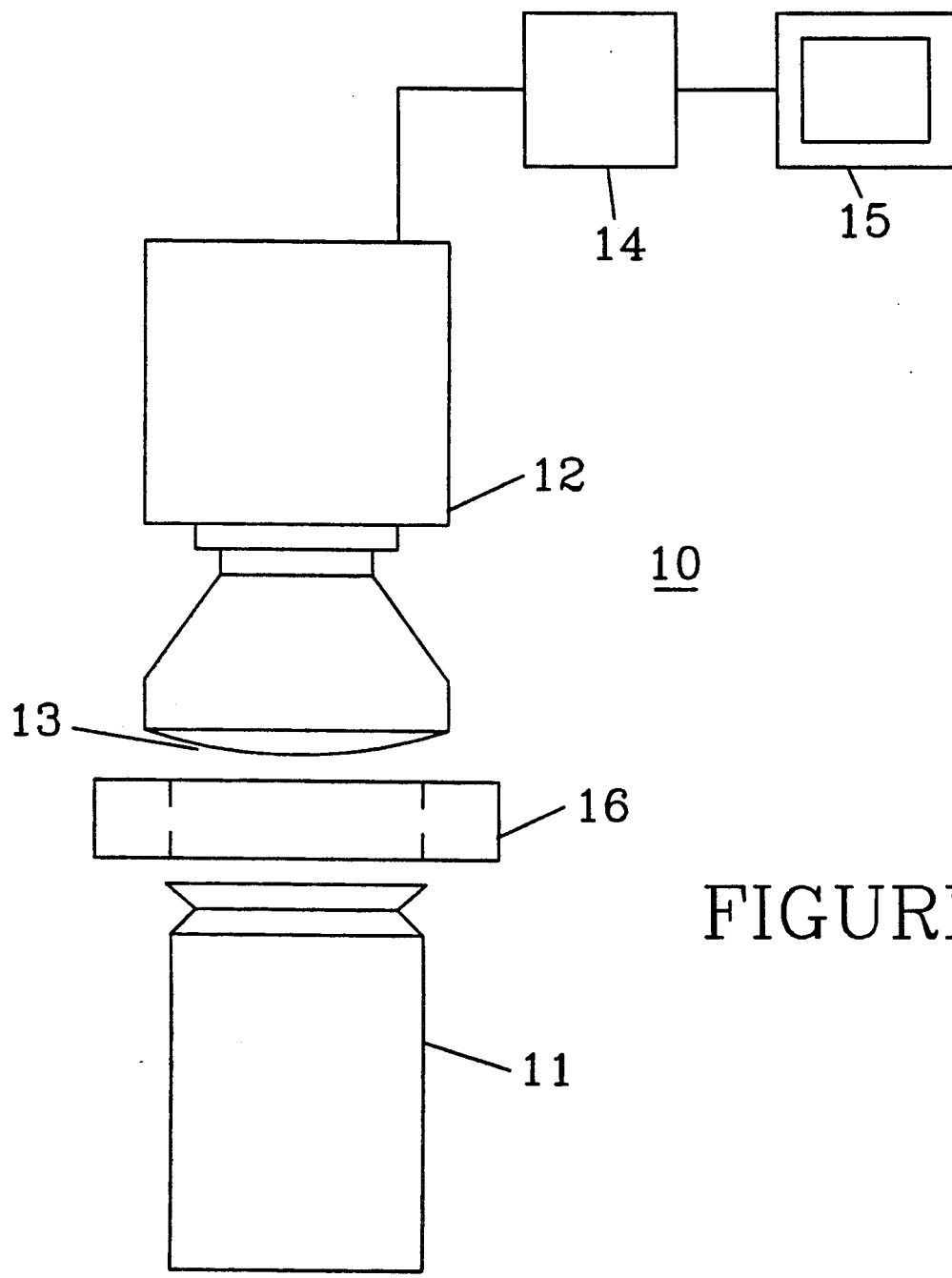
FIG. 1 illustrates a simplified diagram of the container inspection system of the present invention.

FIG. 1 is a simplified illustration of the invention. The machine vision system 10 is used to inspect opaque containers such as beverage can 11. Positioned over can 11 is light source/diffuser 16 which is used to uniformly illuminate the inside of can 11. Camera 12 with lens 13 is positioned over can 11. Lens 13 is positioned above or through the light source/diffuser 16 depending upon the focal length of lens 13. In practice, as will be illustrated and described below, the lens is an extremely short focal length, very wide angle lens that in most applications is positioned through and partially below the light source/diffuser. In FIG. 1, the lens is positioned above the light source/diffuser to clearly illustrate the different components of the system.

Lens 13 may be, for example, a 3.8 mm focal length wide angle lens. The lens angle may be between 110 to 140 degrees, dependent upon the size of the can to be inspected.

Camera 12 may be a high resolution industrial camera such a CCD camera having a resolution from $512 \times 512$ to $1024 \times 1000$ pixels. Such cameras are manufactured by Texas Instruments Incorporated and Sony Corp.

The image viewed by camera 12 is presented to the machine vision processing station 14, which, through software and special hardware functions, inspects the image for defects in the can. The viewed image is displayed on a monitor 15.

Figure 2:
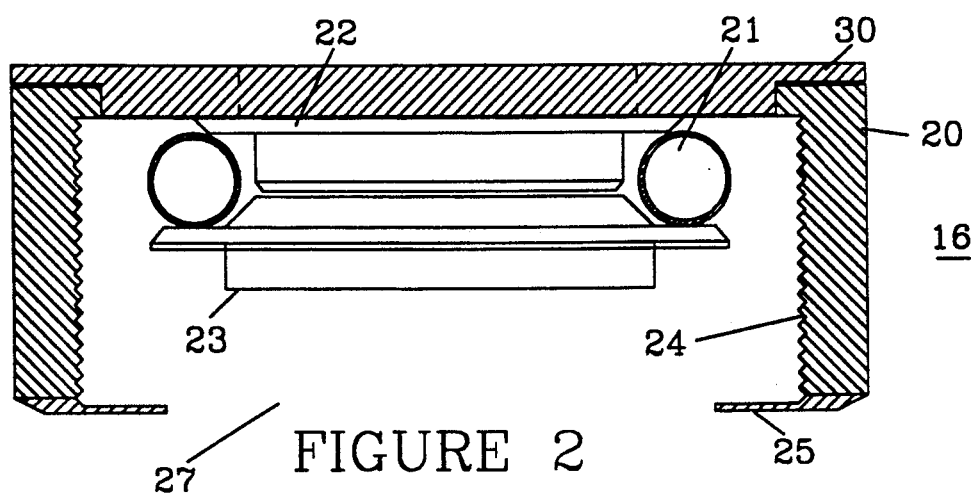
FIG. 2 illustrates the light source and light diffusing system.

FIG. 2 is a simplified view of the light source/diffuser 16. The light source/diffuser includes a housing 20, a lamp 21 and lamp holder 22,23. Lamp 21 is positioned in between holder/mount parts 22 and 23 and held in place by the holder parts. The two parts may be held together by threads wherein lower part 23 and upper part 22 are screwed together after lamp 21 had been placed between the two parts. Alternatively, the two holder parts 22 and 23 may be held together by screws. Lamp mount parts, after assembly, are secured to housing 20 by any convenient means such as screws.

Housing 20 has a diffusing surface 24 which is textured to scatter and evenly diffuse the light from lamp 21 that impinges on the textured surface. The textured surface may be a heavily etched surface or may consist of a series of parallel rings or grooves machined into the surface and extending around the housing inner wall 24. The rings may be independent from each other or may be similar to threads of a threaded surface.

A plate 30 may be mounted over the top of housing 20 so that the light mounting assembly may be secured in place. Plate 30 has an opening 3 therein through which the camera lens may be placed to view the interior of the can.

Figure 3:
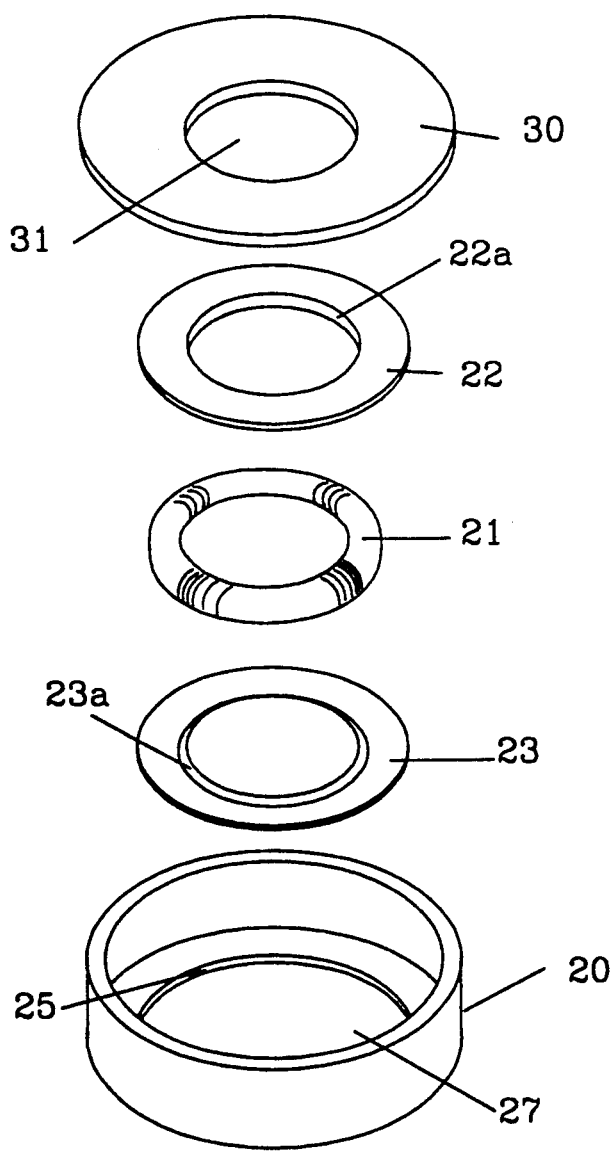
FIG. 3 is an exploded view of the light source and light diffusing apparatus of FIG. 3.

FIG. 3 is an exploded view of the light source/diffuser of FIG. 2. Housing 20 is, for example, round or tubular in shape with an opening in the lower end with the opening defined by lip 25. Lower lamp holder part 23 has a lip 23a at its center periphery which extends up into the circular opening of lamp 21. Upper lamp holder part has a lip 22a that extends down into the circular opening of lamp 21. The two lips 22a and 23a are joined together when the lamp holder is assembled with lamp 21 between the two holder parts. Plate 30 covers the opening at the top of housing 20. Upper lamp holder part 22 may be secured to plate 30 to hold the light housing 20 and the light holder assembly (22,21 and 23) together. Plate 30 has an opening 31 through which the camera lens views the inside of the can to be inspected.

Figure 4:
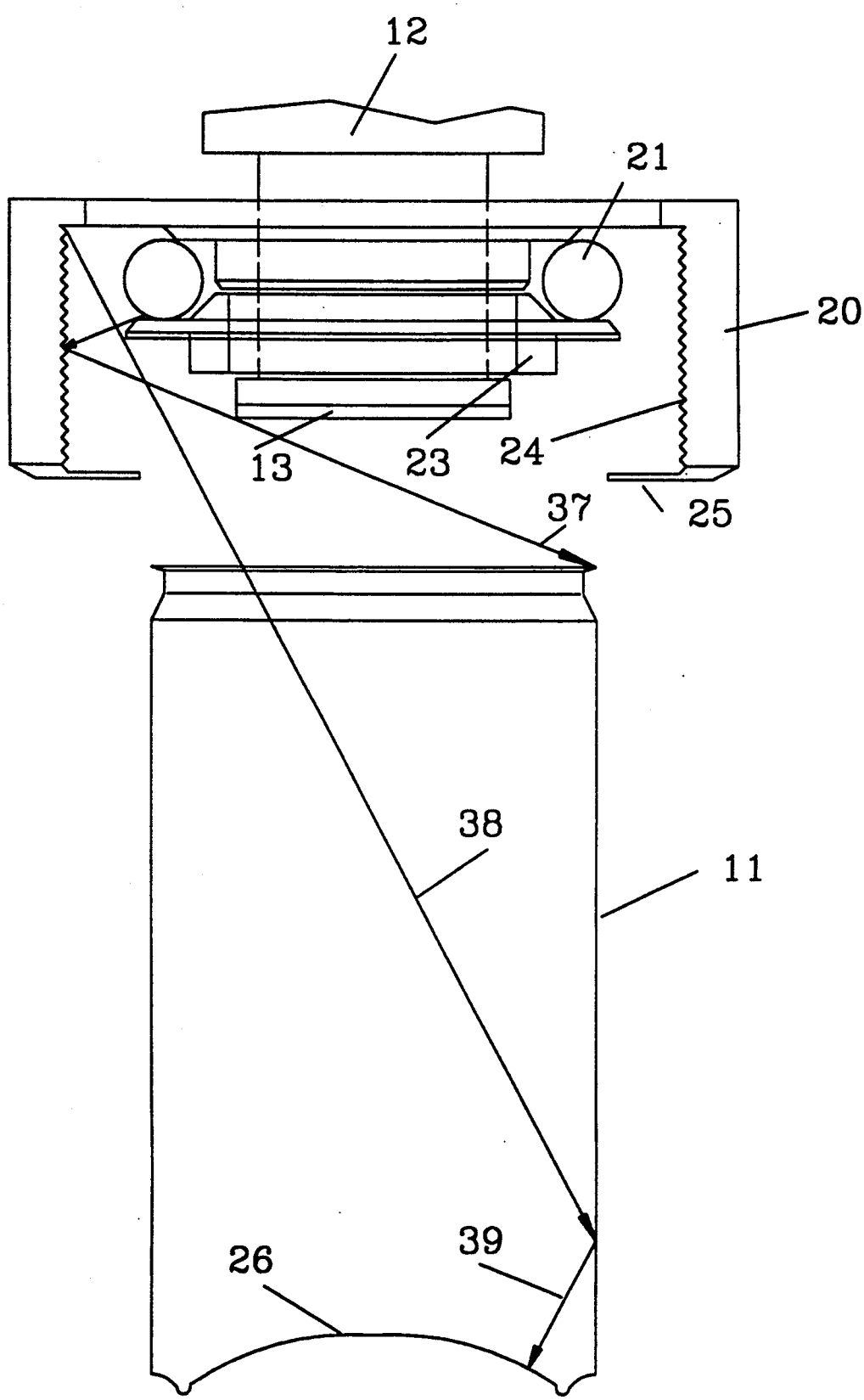
FIG. 4 illustrates an illumination source positioned over a beverage can.

FIG. 4 illustrates the lighting of the inside of the can to be inspected. Light 21 produces illumination that is reflected from the textured wall 24 and reflects it into can 11. Light is not directed directly into the can since lower light mount part 23 blocks direct illumination of the inside of the can. As an example, a first light path 37 is reflected from the diffuser wall 24 and illuminates the upper inside edge of the can 11. Another light path 38 is reflected from diffuser wall 24 to a point on the inside can wall 35 and is reflected to the bottom of the can 36 by light 39. Light impinging on the walls of the can and on the bottom of the can will result in an even distribution of light within the can. Since the light is diffused light, no "hot spots" of light are produced. The position of lens 13 may be raised and lowered with respect to the can to locate the lens, light source and light diffuser to produce uniform lighting within the can.

Lens 13 is a wide angle lens with the lens angle being within the range of 110 to 140 degrees dependent on the can configuration and dimensions. With a lens within this range, the entire can interior walls and bottom may be view at one time. The use of the extremely short focal length in combination with the aperture provides uniform focus from the top to the bottom of the can. By using a high resolution CCD camera, imperfections or foreign particles may be easily detected.

What is claimed:

1. A single camera container inspection system for imaging the entire interior of the container in one pass, comprising:
    a reflected light diffuser light source assembly for indirectly illuminating the entire interior of the container, the reflected light diffuser/light source assembly has a vertical, wall having concentric grooves therein for reflecting defused light from the light source into the container being inspected;
    a high resolution camera positioned to view into the container; and
    a short focal length, wide angle lens on the camera capable of viewing the entire interior of the container at one time.

2. The inspection system according to claim 1, wherein the wide angle lens has an angle from about 110 degrees to about 140 degrees.

3. The inspection system according to claim 1, wherein the high resolution camera is a CCD camera and has a resolution from about 512×512 pixels to 1024×1000 pixels.

4. The inspection system according to claim 1, wherein the reflected light diffuser/light assembly includes a light mount assembly that prevents light from the light source from directly illuminating the inside of the container being inspected.

5. The inspection system according to claim 1, wherein the reflected light diffuser/light source assembly has a vertical, textured wall for reflecting defused light from the light source into the container being inspected.

6. The inspection system according to claim 1, wherein the camera lens extends through the light source/diffuser assembly to a position adjacent the top of the container being inspected.

7. The inspection system according to claim 1, including a machine vision image processing system for automatically analyzing the image of the entire interior surface of the container being inspected to detect defects and contaminants in the container walls and bottom.

8. The inspection system according to claim 7, including a monitor to display the entire interior surface of the container at one time to provide a visual image of the inside surface of the container.

9. The inspection system according to claim 1, wherein reflected diffused light and re-reflected diffused light is used to uniformly illuminate the entire interior surface of the container at one time.

* * * * *